(12) United States Patent
Wikfors et al.

(10) Patent No.: US 7,670,487 B2
(45) Date of Patent: Mar. 2, 2010

(54) DE-PRESSURIZATION SCHEME FOR CHROMATOGRAPHY COLUMNS

(76) Inventors: Edwin E. Wikfors, 13 Hill Crest Dr., Landenberg, PA (US) 19350; Kimber D. Fogelman, 710 Lorna La., Hockessin, DE (US) 19707

( * ) Notice: Subject to any disclaimer, the term of this patent is extended or adjusted under 35 U.S.C. 154(b) by 893 days.

(21) Appl. No.: 11/490,498

(22) Filed: Jul. 21, 2006

(65) Prior Publication Data

US 2008/0021663 A1 Jan. 24, 2008

(51) Int. Cl.
*B01D 15/08* (2006.01)
(52) U.S. Cl. .................. 210/198.2; 210/137; 210/143; 210/635; 210/656
(58) Field of Classification Search ............... 210/634, 210/635, 656, 659, 198.2, 137, 143
See application file for complete search history.

(56) References Cited

U.S. PATENT DOCUMENTS

| | | | |
|---|---|---|---|
| 3,440,864 A | 4/1969 | Blume | |
| 4,350,595 A | 9/1982 | Gunkel | |
| 4,451,364 A | 5/1984 | Higgins et al. | |
| 4,522,715 A | 6/1985 | Walters | |
| 4,551,249 A | 11/1985 | Shackelford et al. | |
| 4,565,632 A | 1/1986 | Hatch et al. | |
| 4,587,014 A | 5/1986 | America | |
| 4,591,442 A * | 5/1986 | Andrews | 210/656 |
| 4,845,985 A | 7/1989 | Berger | |
| 4,871,453 A * | 10/1989 | Kumar | 210/198.2 |
| 5,094,741 A * | 3/1992 | Frank et al. | 210/198.2 |
| 5,171,440 A | 12/1992 | Kawamura | |
| 5,322,626 A * | 6/1994 | Frank et al. | 210/634 |
| 5,324,426 A | 6/1994 | Joseph et al. | |
| 5,338,448 A | 8/1994 | Gjerde | |
| 5,472,612 A * | 12/1995 | Maxwell | 210/634 |
| 5,651,885 A | 7/1997 | Schick | |
| 6,294,087 B1 | 9/2001 | Hargro et al. | |
| 6,352,266 B1 | 3/2002 | Rigoli | |
| 6,648,609 B2 * | 11/2003 | Berger et al. | 417/297 |
| 6,843,918 B2 * | 1/2005 | Hauck et al. | 210/656 |
| 7,267,765 B2 * | 9/2007 | Hauck et al. | 210/198.2 |
| 7,402,251 B2 * | 7/2008 | Mann et al. | 210/656 |
| 2004/0016701 A1 * | 1/2004 | Hauck et al. | 210/656 |
| 2005/0087494 A1 * | 4/2005 | Hauck et al. | 210/656 |
| 2007/0144955 A1 * | 6/2007 | Mann et al. | 210/198.2 |

\* cited by examiner

*Primary Examiner*—Ernest G Therkorn
(74) *Attorney, Agent, or Firm*—Meyer, Unkovic & Scott LLP; David G. Oberdick

(57) ABSTRACT

A depressurization process for a packed separation column is provided where the column system experiences a rapid and/or severe drop in pressure that could potentially damage column components. The process provides a safe de-pressurization of the column on the outlet side by decreasing the outlet pressure in controlled steps while allowing the inlet pressure of the column time to lower after each decreased step.

7 Claims, 5 Drawing Sheets

DE-PRESSURIZATION SCHEME FOR CHROMATOGRAPHY COLUMNS

FIELD OF THE INVENTION

The present invention relates to a process for controlled de-pressurization of a separation column in a chromatography system.

BACKGROUND OF THE INVENTION

In the technology of chromatography, the separation and collection of fractions of chemical compounds vary in process, instruments, and production capability. However, each type of system uses at least a fluid, called a mobile phase, that is pumped into the head of a separation column. A sample containing one or more chemical compounds is carried by the mobile phase flowstream through the column. The media in a column delays certain compounds from exiting the outlet of the column according to different retention times. These separated compounds can be detected and graphed as a "peak" of the injected sample. If the same temperature, pressure, flowrate, and injection composition is maintained in the chromatography system, then repeated injections into the column of the same mixture can produce repeated peaks of the same compounds exiting the column. These eluted peaks contain purified samples that can be collected in a collection system.

The parameters and instruments of the chromatography system can be adjusted in order to optimize the speed, efficiency, and accuracy of analyte collection. An advancement of liquid chromatography (LC) is HPLC (High Performance Liquid Chromatography), which uses 20 mm to one inch diameter columns with flowrates optimized at 20 to 30 ml/min. While process and collection speeds are faster than LC, drawbacks to HPLC include high waste solvent production and slow effective process time for samples due to removal of solvent and water from collected sample fractions.

For many applications, an alternative separation technology called supercritical fluid chromatography (SFC) has advanced past other chromatography technologies. SFC uses highly compressible mobile phases, which typically employ carbon dioxide (CO2) as a principle component. In addition to CO2, the mobile phase frequently contains an organic solvent modifier, which adjusts the polarity of the mobile phase for optimum chromatographic performance. Since different components of a sample may require different levels of organic modifier to elute rapidly, a common technique is to continuously vary the mobile phase composition by linearly increasing the organic modifier content. This technique is called gradient elution.

SFC has been proven to have superior speed and resolving power compared to traditional HPLC for many applications. This results from the dramatically improved diffusion rates of solutes in SFC mobile phases compared to HPLC mobile phases. Separations have been accomplished as much as an order of magnitude faster using SFC instruments compared to HPLC instruments using the same chromatographic column. A key factor to optimizing SFC separations is the ability to independently control flow, density and composition of the mobile phase over the course of the separation. SFC is finding significant advantages in the separation of enantiomers and is supplanting normal-phase HPLC for performing chiral separations.

Conventional LC columns, during manufacture, are constructed with end fittings such as a frit that act to retain the packing material inside the column. The packing media material is loaded to completely fill the column and retained at both ends by the fittings that each include a frit element. The frit acts as both a seal to hold the packing media inside the column and as a radial distribution element to distribute the incoming fluid substantially evenly across the cross-section of the column. In some commercial columns, the frit is initially press-fit into the fitting prior to the fitting being placed on the end of the column. In the prior art, columns are often machine tooled at the ends, which causes stresses and weakening at the ends that can cause premature breakage.

Problems occur with chromatography columns that are caused by rapid and/or uncontrolled pressure loss occurring downstream of the outlet side of the column in a process system. If the mobile phase flowstream contains a gas liquefied under pressure, such as carbon dioxide, then rapid depressurization will cause the gas to rapidly evaporate and freeze and in the case of carbon dioxide freeze form dry ice. The pressure differential between the inlet at full pressure and outlet at atmospheric pressure in a column can be as high as 100 bar. Expanding gas throughout the column media bed builds tremendous pressure forces against the outlet of the column. Since frits are commonly metal that are fitted into a column with a plastic ring, the freezing of the metal and the freezing of the plastic ring will cause differential swelling between the frit and its fittings. Further, if pressure is instantly relieved in a column of packed media bed containing a flowstream of carbon dioxide, dry ice will form in the media bed itself and disturb the packing consistency of the bed. The combination of differential shrinking of the frit and fittings and disturbance in the bed caused by expanding mobile phase under pressure force towards the column outlet could cause loss of packed media past the frit.

The instant release of pressure from an expanding mobile phase in a column can also damage the frit itself. A frit that is instantly frozen by dry ice becomes brittle, and its channels normally used for distributing fluid flowstreams become clogged up with dry ice, which blocks all flow out of the column. With a clogged outlet to the column and the column media still under rising high pressure, the failure of the frit along with damage to column media can occur. In larger columns, the larger diameter frit is even more susceptible structural to deflection caused by clogging and pressure from the packed media. A larger frit has less structural support at its center. If the frit freezes and becomes brittle, it can crack or break upon deflection from the upstream pressure forces attempting to escape the column. Further, the pressure differential between the ends of the column can cause an impulse force directly onto the frit whether or not the channels in the frit freeze, causing potential failure of the frit and its fittings.

SUMMARY OF THE INVENTION

The preferred and alternative embodiments overcome the problems described above of potential damage to separation columns, such as a packed chromatography column, caused by rapid or severe pressure loss. The preferred embodiment is a process for de-pressurization of the column after such a pressure loss has occurred and the system has stopped pumping mobile phase into the column. Once flow from the pump has ceased, the flowstream in the column is in a static condition from the lack of pressure forces and flow from the pump. The remaining pressure causing flow out of the column is due to expansion of the mobile phase caused by the decrease in pressure, not because of pressure applied by pumps. The outlet pressure of the column is adjusted so that the expansion of the flowstream that occurs at pressure loss can be controlled to flow out of the column. The de-pressurization scheme decreases column outlet pressure in steps that each maintain outlet pressure for time period before decreasing the pressure to the next pressure setpoint. This process allows the inlet pressure of the column to decrease at a controlled rate of decrease of the outlet pressure. The decrease in pressure with setpoints reduces the negative effects of rapid pressure loss on the column and thereby reduces potential failure and damage to the column.

The effect of the controlled de-pressurization is to avoid any rapid expansion of the mobile phase in the column. It also avoids freezing the packed media, frit, fittings, and then subjecting them to a high pressure force caused by uncontrolled expansion of the gas in the mobile phase exposed to lower pressures.

BRIEF DESCRIPTION OF THE DRAWINGS

For a better understanding of the nature of the present invention, its features and advantages, the subsequent detailed description is presented in connection with accompanying drawings in which.

DETAILED DESCRIPTION OF THE INVENTION

Figure 1:
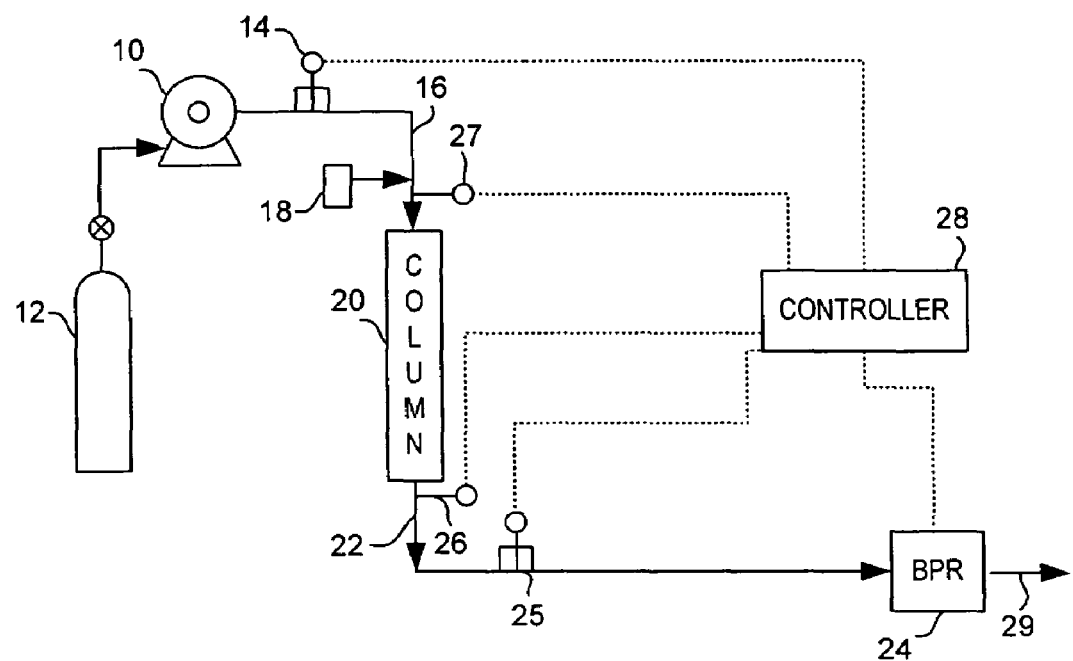
FIG. 1 illustrates components of a chromatography system that implements the method of the preferred embodiment.

FIG. 1 illustrates a preferred chromatography system implementing the de-pressurization process of the preferred embodiment. The figure shows a chromatography system, such as a liquid chromatography (LC), gas chromatography, high performance liquid chromatography (HPLC), or supercritical fluid chromatography system. However, it is understood that any system utilizing a device handling a mobile phase flowstream under pressure with a potential for damage to the device if pressure is lost could benefit from the present invention.

The system includes at least one pump 10 to draw liquid or gaseous mobile phase from one or more tanks 12. Pump 10 may include multiple pumps drawing from different tanks of modifier liquid and gas for mixing as a mobile phase fluid at high or supercritical pressure conditions. Depending upon the type of chromatography system, mobile phase can be pure or modified fluids including binary and tertiary fluids containing additives. As examples, pure fluids include but are not limited to: carbon dioxide, nitrous oxide, sulfur hexafluoride flouroform, etc. Modified fluids include: methanol, or other alcohols, acetonitrile, tetrahydrofuran, hexane, and others mixed with one of the fluids above. Modified fluids can contain more than one modifier or more than one main fluid or both more than one modifier and more than one fluid. Tertiary fluids may include any of the mixtures under modified fluids above with the addition of polar additives such as trifluoroacetic acid, isopropylamine among others known in the art. Typical concentrations of modifier range from zero to approximately 50% of the mobile phase but can be more.

In normal operating conditions, pump 10 feeds the mobile phase under pressure through dampener and pressure transducer 14 on transfer line 16 prior to entering packed chromatography column 20. The column structure may be one continuous packed column but could have multiple columns connected in series. During sample injection and separation processes, injection valve 18 injects a liquid sample into the flowstream at the head of column 20. Sample analytes, or components, are separated by packed media within column 20 according to each component's retention time in the column 20. Regardless of the mixture of mobile phase, there should be a single phase of fluid throughout the column. Sample eluants exit column 20 under pressure due to backpressure regulator (BPR) 24 maintaining pressure upstream in line 22 and column 20. In an SFC system, expanded elution fluid leaves the backpressure regulator 24 at a velocity of approximately two to five times the flow velocity upstream of the BPR 24. After passing BPR 24, the flowstream is typically directed to a collection system, waste stream, or further processing (not shown).

The preferred process controls pressure at the column 20 outlet. To accomplish this, a valve 25, such as a pressure transducer, is located on line 22, which is downstream of the outlet side of column 20. Further, an outlet pressure sensor 26 to measure $P_{out}$ is located at the outlet side of column 20 or a flowline on the outlet side and an inlet pressure sensor 27 to measure $P_{in}$ is located at the inlet of column 20 or on a flowline on the inlet side. Controller 28 is operatively connected to at least pressure sensors 26 and 27, transducers 14 and 25, pump 10, injection valve 18, and BPR 24. Controller comprises a chromatography process control computer as known in the art that comprises one or more computer processors, soft and hard memory, logic, software for recording and analyzing data from system components, and user interface and display devices. A processor in the controller is used to analyze information from, and control the operation of, outlet pressure control transducer 25.

Figure 2:
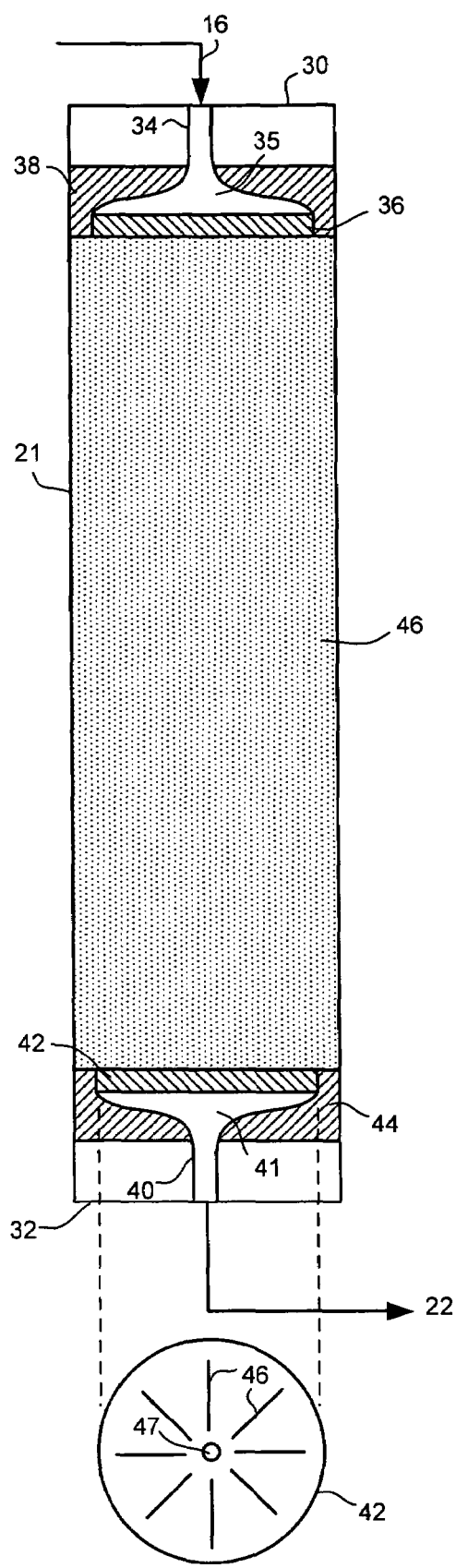
FIG. 2 illustrates a more detailed view of an exemplary chromatography column of FIG. 1.

A longitudinal cross-sectional diagram of packed column 20 is illustrated in FIG. 2. Column 20 includes a tubular housing 21 filled with packed media material 46 used in chromatography columns. Packing media can include silica, alumina, or other known, suitable materials. The packing may be totally porous or beads with a porous coating of a hard (non-porous) interior. Known bonded phases may be applied to the particles. The packing particles will usually have an average particle diameter between about 0.5 micron to 50 microns, preferably about 1.5 microns to 10 microns. Columns used for SFC are mainly silica based with small, totally porous particles. The most typical use spherical 5 micrometers particles with 60-300 Å pores, 150-500 $m^2$/g surface area, packed in stainless steel tubes 10-25 cm long, 1-6 mm ID.

The column housing 21 is typically constructed of rigid, strong metal such as stainless steel or an aluminum alloy. Tubular housing 21 includes a first end part 30 at the column head, wherein mobile phase enters the column 20 and a second end part 32 at the column outlet, where mobile phase exits the column. Packed media 46 is held inside the housing 21 by a first seal 38 at the first end and a second seal 44 at the second end. Each seal exerts pressure on the packed media 46 by direct contact. A seal 38, 44 is typically constructed of a rigid plastic material and includes a series of grooves or striations on its outer surface. A transfer tube 34 connects to transfer line 16. Tube 34 flares into an open chamber 35 that contains a filter in the form of a frit 36 that distributes mobile phase passing through to the packed media 46. Frit 35 is also held in place by seal 38. Similar column components are assembled at the outlet end 32 of column 20. Frit 42 and packed media 46 are held in place by seal 44. Tube 40 receives mobile phase from the frit 42 through a chamber 41 that flares down into tube 40 and connects to transfer line 22.

As separation columns in chromatography are designed with larger and larger dimensions, particularly in SFC, the packed media in a column as stationary phase is typically held in the column ends by frits. The frit materials of construction are typically sintered metal or polymer. Each frit is generally supported near the inner edges of the column housing but is either not supported or has far less structural integrity towards the center of the frit from the edges. A cross-sectional view of frit 42 is shown in the exploded diagram below column 20 in FIG. 2. Frit 36 would typically be formed similar to frit 42. Frit 42 is formed as a disk having a diameter smaller than the inner diameter (ID) of tube housing 21 to allow secure placement inside the column housing 21 and could be threaded on the outer edge to engage a threaded area of seal 44 inside housing 21, depending on the construction of the column. Several radial points 46 and a center hole 47 are typically formed in the frit 42 to allow for distributed flow of mobile phase through the frit. At the column inlet end 30, frit 36 provides distributed flow into packed media 46 to prevent channeling, and at the second end 32, frit 42 receives the distributed flow from packed material 42 for the same purpose. The chamber 41 does not support the actual frit 42 itself, but if the flared part is not formed on the frit, then mobile phase does not drain cleanly from the entire cross-section of the packed media 46. As is understood by one skilled in the art, although a frit 42 is shown and described in the preferred embodiment, the present invention could apply to a column that implements dispersion filters in a column other than or in addition to frits.

As stated previously, a problem occurs in larger diameter columns the outlet frit is subject to high pressure loads of the flowstream as well as structural loads to keep the packed media held in a column. If outlet pressure rapidly or uncontrollably drops during separation processes and causes gas in the mobile phase to rapidly evaporate, the column and its components will be susceptible to freezing and blockage by dry ice. Under such conditions the frit 42 and seal 44 will have differential shrinkage due to the different rates of cold shrinkage between a plastic seal and metallic frit. The main pressure force caused by a pressure drop in the column is focused on the outlet frit 42 since expanding mobile phase will follow the linear path of flow, these effects can cause deflection that will upset the column packed media bed and cause channeling within the column.

Figure 3:
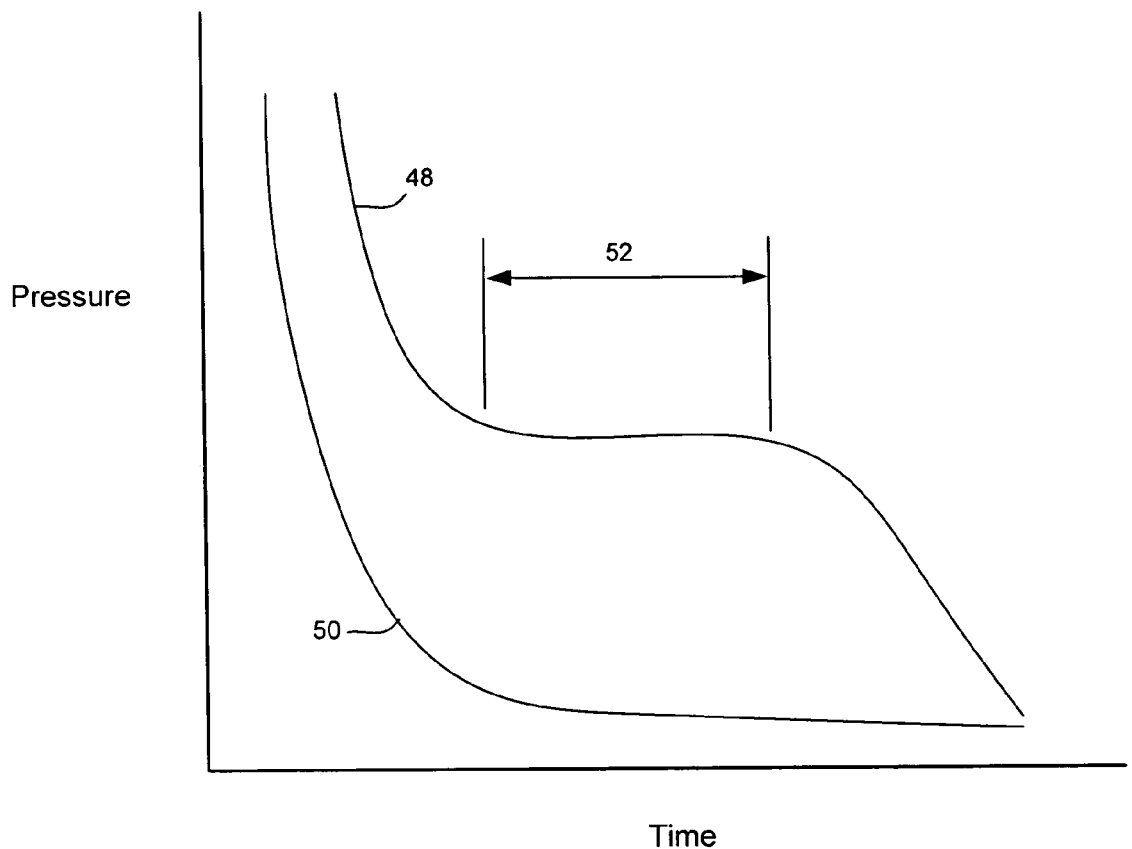
FIG. 3 illustrates a graph of inlet and outlet pressures of a chromatography column after severe de-pressurization in the prior art.

A graphical representation of a known pressure drop at $P_{out}$ on the column 20 outlet that occurred after a severe and/or rapid pressure drop at the outlet over time is shown in FIG. 3. The graphed line 50, representing pressure at the outlet of the column, falls rapidly, representing a release of the pressure inside the column and then flattens off where the mobile phase within the column expands out of the column. Graphed line 48 represents the pressure at the head of column 20 during the period when a decrease in outlet 32 pressure has decreased significantly. Upstream pressure on line 48 can be as high as 280 to 300 bar in an SFC system at the head of the column and 100 bar starting on line 50 at the outlet 32 of the column, leaving a pressure differential of up to 200 bar across the column 20. If inlet flow to column 20 is stopped, then the pressure at the head of the column will drop to 100 bar and if the BPR 24 is turned off thereby releasing all pressure downstream of the column represented by trace 50 dropping rapidly, the pressure at the column head 30 will drop as quickly as possible to atmospheric, represented by the trace 48 that drops quickly and then levels off over time.

A rapid pressure loss in the column also causes more problems in an SFC system than in other chromatography systems. If the system is using a mobile phase that includes carbon dioxide, for example, the drop from 100 bar of pressure at column outlet 32 to near zero will evaporate the liquefied carbon dioxide of the mobile phase rapidly inside of column 20. The carbon dioxide then freezes to dry ice in the column and on its components. The inlet 30 pressure decreases much slower and remains in graphed pressure region 52 for a longer period of time as liquid carbon dioxide changes to gas. The pressure differential inside the column can reach 60 to 80 bar and becomes an impulse force directly across the frit 42.

Figure 4:
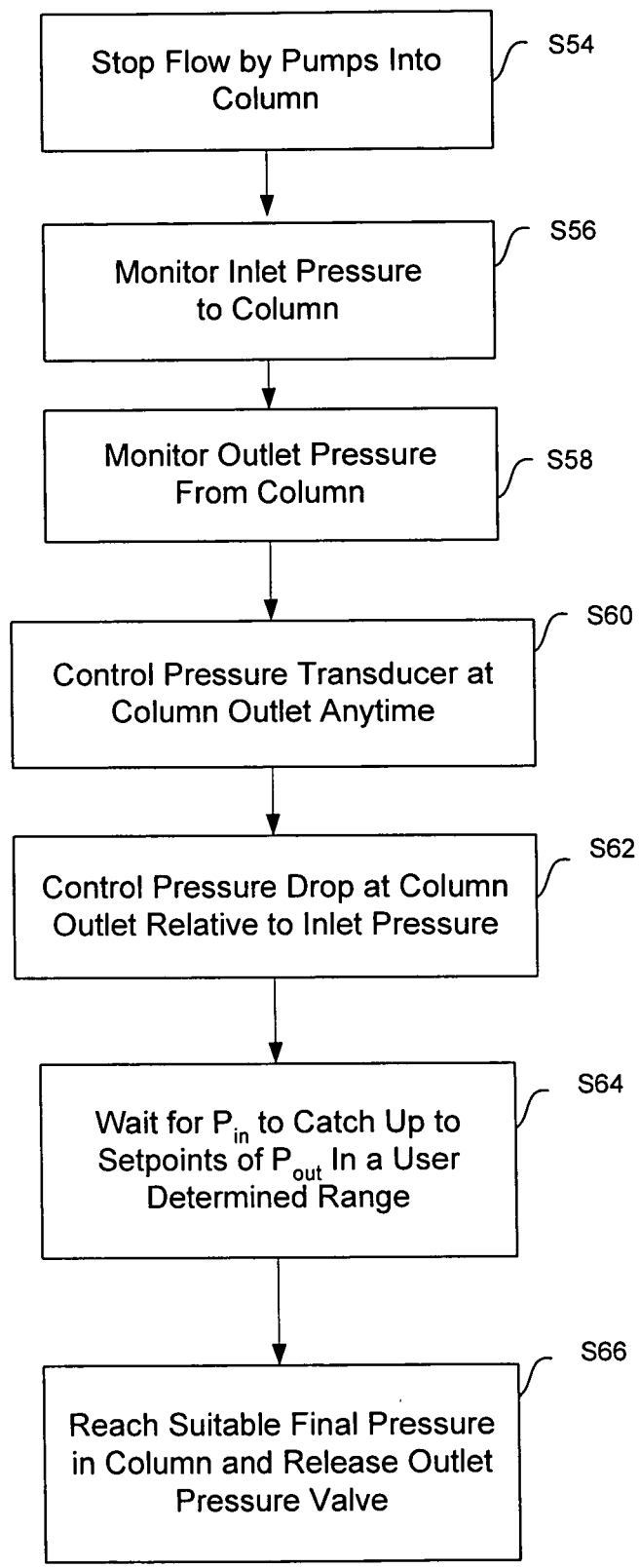
FIG. 4 illustrates a flowchart of a process of the preferred and alternative embodiments.
Figure 5:
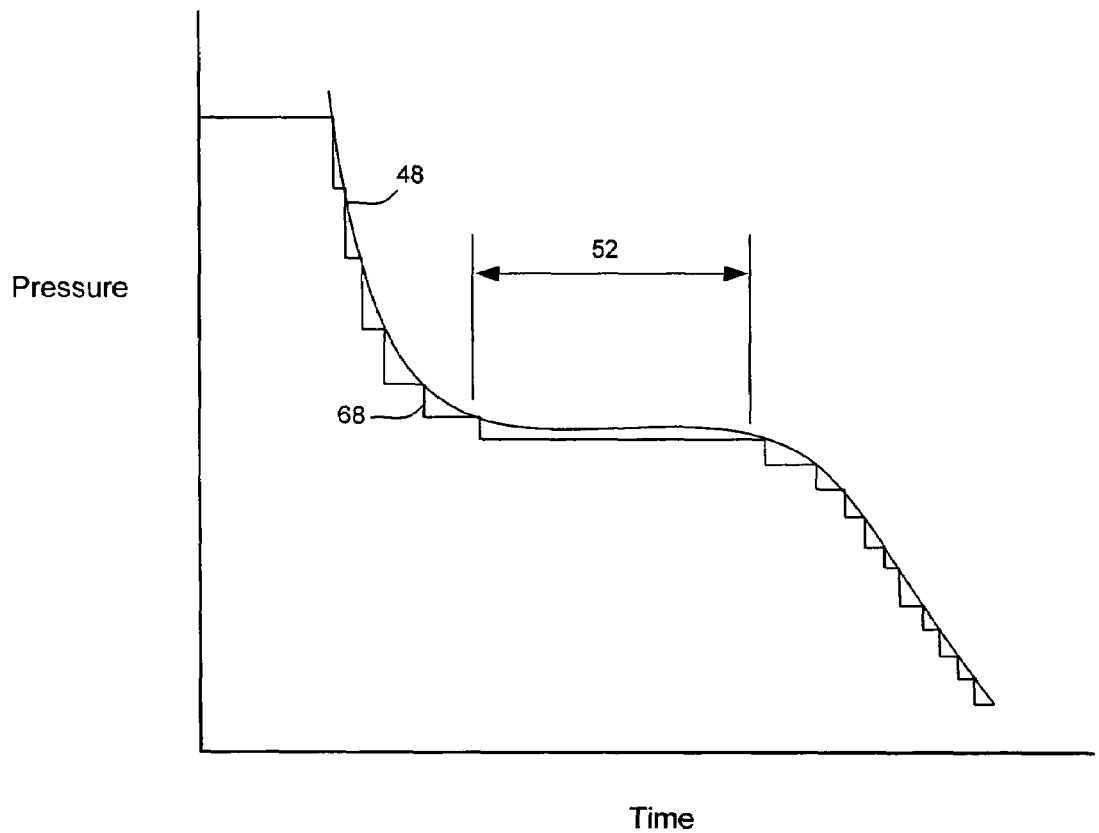
FIG. 5 illustrates a graph of inlet and outlet pressures of a chromatography column controlled by the preferred embodiment after severe de-pressurization.

The preferred embodiment of the system for de-pressurization is shown in FIG. 1 and the preferred embodiment of the process for de-pressurization is illustrated in the flow chart of FIG. 4 and the graph in FIG. 5. The controller 28 monitors for a rapid pressure drop in pressure of column 20 that could potentially damage column components. The range of potentially damaging pressure drops can be determined by the system manufacturer or operator and/or the column manufacturer. The preferred process is performed at relatively static conditions of the flowstream. This means that when a rapid and/or severe pressure drop is detected S58 at column 20, the controller 28 turns pump 10 off S54 thereby stopping further flow from entering column 20. However, the preferred process can be implemented anytime pump 10 stops operating or anytime pressure drops in the system for any reason. Once the flowstream is stopped S54 and the flowstream inside column 20 is subjected to significantly lower pressure or atmospheric pressure, gas dissolved in the mobile phase flowstream will rapidly expand and continue expanding in the normal direction of flow of the column 20. Inlet pressure sensor 27, located on the inlet side of column 20, is used by controller 28 to monitor and record S56 the inlet pressure $P_{in}$ at or upstream of the inlet 30 of column 20. Outlet pressure sensor 26, located on the outlet side of column 20, is used by controller 28 to monitor and record S58 outlet pressure $P_{out}$ at or downstream of the outlet 32 of column 20.

To physically control the expanding mobile phase flowstream in column 20, a valve 25, such as a pressure transducer, is located at or in the flowline downstream of the outlet 32 of column 20. One skilled in the art knows that other pressure and valved devices or a combination of valves and sensors could be used in the preferred embodiment in place of transducer 25 without varying from the scope of the present invention. Transducer 25 may contain pressure sensors on its upstream and downstream sides that are monitored by controller 28 to determine flowstream pressure conditions at the transducer itself. At static conditions in the column 20, controller 28 prevents S60 the expanding flowstream from rapidly exiting column 20 using pressure transducer 25 to repeatedly lower S62 the pressure drop $P_{out}$ at the column outlet 32 relative to the column inlet pressure $P_{in}$. Feedback from the monitoring inlet S56 and outlet S58 column pressures can be used to dynamically set the points of lower pressure and/or use a range of lower pressure setpoints.

The de-pressurization scheme decreases column outlet pressure gradually so that the expansion of the flowstream in the column can safely flow through the outlet. After pump 10 stops and static conditions are set in the column 20, the controller maintains pressure transducer 25 to hold outlet pressure $P_{out}$ for a time period and monitors for the column inlet pressure $P_{in}$ to stabilize at or within a range of pressure relative to the pressure at $P_{out}$. Outlet pressure is then lowered and held at the lower pressure setpoint for a time period S64 to allow $P_{in}$ to drop correspondingly. The pressure at $P_{in}$ may not drop to the new lower pressure setpoint $P_{out}$. The time lag between setting $P_{out}$ to a lower pressure setpoint and $P_{in}$ lowering to a range relative to the new lower pressure setpoint will vary according to volume and type of packed media bed, volume and composition of the flowstream left in the column, pressure in the column, and range of the setpoint, among others. Since $P_{in}$ and $P_{out}$ are monitored, the lag time for $P_{in}$ to catch up to a lowered setpoint of $P_{out}$ can be analyzed and recorded.

Pressure setpoints for $P_{out}$ are defined by the system operator and can vary according to pressure, time, or any other user-defined parameter. Ranges for pressure drops in $P_{in}$ to meet as a result of a lowered setpoint for $P_{out}$ are also user-definable. Once $P_{in}$ drops to within the defined range of lower pressure, the $P_{out}$ is lowered-to the next consecutive setpoint. In an alternative method, the time lag for $P_{in}$ to drop within a range of a new $P_{out}$ setpoint is assumed and the setpoints for $P_{out}$ are each lowered at the assumed time periods. A user can program controller 28 to insures that the change in pressure between $P_{in}$ and $P_{out}$ during a de-pressurization does not exceed a certain safety limit or a certain range in the setpoints in order to prevent damage to the column 20.

The process of lowering setpoints for $P_{out}$ and waiting for $P_{in}$ to drop is repeated over time until pressure at $P_{in}$ reaches a suitable final pressure S66, after which the pressure transducer 25 can be released open. The pressure setpoints are lowered in a series of steps of pressure drops that are illustrated as line 68 in the graph shown in FIG. 5. The graph outlet pressure drop steps 68 is exaggerated for illustrative purposes. Column outlet pressure $P_{out}$ series of setpoints is can be set to approximately track the former pressure drop graph 48 over time. Each lowered setpoint in outlet pressure drop 68 can be very small, such as fractions of a pound per square inch drops multiple times a second, or could vary according to user programming to pounds per square inch over an empirically determined time period. The ranges of setpoints and ranges of pressures for decreases at each setpoint should be selected so that a mobile phase pressure drop in the column follows the pressure drop 68 without damaging column 20 components. The setpoints following pressure $P_{out}$ shown in line 68 should maintain an approximate minimum and maximum interval of pressure difference between inlet 30 and outlet 32 during the controlled depressurization.

Although a controlled linear rate of de-pressurization is possible as an alternative, such a method would not take into account the period of flatness 52 in the depressurization graph of the inlet pressure drop 48, where the inlet column pressure slows or stops decreasing over time. In other words, there is a period represented in the graph as range 52 where decreasing the outlet pressure has a much lesser effect on the drop in the inlet pressure.

An advantage of the present invention is that the de-pressurization of a column can save a separation column and its packed media bed from damage associated with severe drops in flowstream pressure during a process run. Some columns in chromatography cost over US $50,000 and therefore damaging a column presents a costly expense. The present invention can apply to any system using separation columns and is particularly suited to SFC and SFE systems where high pressures and gas used in the mobile phase present greater chances for damage to a column.

One skilled in the art will appreciate that the present invention can be practiced by other than the described embodiments, which are presented for purposes of illustration and not limitation, and the present invention is limited only by the claims that follow.

What is claimed is:

1. A system for de-pressurization of a separation column containing a mobile phase in a static flow state, comprising:
   a separation column comprising an inlet flowline connected to a pump, wherein the pump has stopped pumping a mobile phase flow into the column;
   a valve connected on an outlet flowline of the separation column;
   an inlet pressure sensor connected to the inlet flowline of the column and an outlet pressure sensor connected to the outlet flowline of the column;
   a controller, comprising a computer with memory and a processor, operatively connected to the pressure valve, inlet pressure sensor, and outlet pressure sensor,
   wherein the controller performs:
   monitoring of an inlet pressure and an outlet pressure of the mobile phase within the column;
   decreasing the outlet pressure to a pressure setpoint; and
   maintaining the outlet pressure setpoint for a time period until the inlet pressure decreases to within a range of the outlet pressure setpoint.

2. The system of claim 1, wherein the decreasing comprises setting consecutive outlet pressure setpoints, and
   wherein the size of each consecutive setpoint is set by a controller of outlet pressure of the column.

3. The system of claim 2, wherein the setpoints are decreased over time in a series that tracks a known column outlet pressure drop that occurred after a severe or rapid pressure loss in the column.

4. The system of claim 1, wherein the decreasing comprises maintaining a range of pressure difference between the inlet pressure and the outlet pressure.

5. The system of claim 1, wherein the decreasing comprises decreasing the outlet pressure to a range of pressures around the pressure setpoint.

6. The system of claim 1, wherein the decreasing and the maintaining are repeated until the pressure of the mobile phase within the column is reduced to a suitable final pressure.

7. The system of claim 1, wherein the method for de-pressurization of the mobile phase comprises de-pressurizing the separation column containing the mobile phase of a liquefied gas or supercritical fluid under pressure.

* * * * *